(12) United States Patent
Feiweier

(10) Patent No.: US 6,841,997 B2
(45) Date of Patent: Jan. 11, 2005

(54) MAGNETIC RESONANCE METHOD AND APPARATUS FOR GENERATING RESPECTIVE IMAGES FROM SPIN ENSEMBLES EXHIBITING DIFFERENT CHEMICAL SHIFT

(75) Inventor: Thorsten Feiweier, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 343 days.

(21) Appl. No.: 10/144,105

(22) Filed: May 13, 2002

(65) Prior Publication Data
US 2002/0193680 A1 Dec. 19, 2002

(30) Foreign Application Priority Data
May 11, 2001 (DE) .......................................... 101 22 874

(51) Int. Cl.[7] .................................................. G01V 3/00
(52) U.S. Cl. ...................................... 324/307; 324/309
(58) Field of Search ................................ 324/307, 309, 324/306, 312, 314, 318, 322, 300

(56) References Cited

U.S. PATENT DOCUMENTS 6,091,243 A * 7/2000 Xiang et al. ................. 324/307
6,263,228 B1 * 7/2001 Zhang et al. ................. 600/409
6,466,014 B1 * 10/2002 Ma ............................. 324/307
6,483,308 B1 * 11/2002 Ma et al. ..................... 324/312
6,603,990 B2 * 8/2003 Zhang et al. ................. 600/410

FOREIGN PATENT DOCUMENTS

GB    2 320 576    6/1998

OTHER PUBLICATIONS

"Simple Proton Spectroscopic Imaging," Dixon, Radiology, vol. 153 (1984) pp. 189–194.

* cited by examiner

Primary Examiner—Louis M. Arana
(74) Attorney, Agent, or Firm—Schiff Hardin & Waite

(57) ABSTRACT

In a nuclear magnetic resonance tomography apparatus and a method for the operation thereof, on the basis of the 3-point Dixon method, spin collectives having different chemical shifts are separated by means of information maximization despite great field inhomogeneities. The unwrapping of the phases is implemented over interconnected pixel regions (phase unwrapping) proceeds initially only in regions with high signal amplitude and the regions of lower amplitudes are only successively acquired by increments. These are then assigned to the respectively correct spin type, such as fat or water.

34 Claims, 4 Drawing Sheets

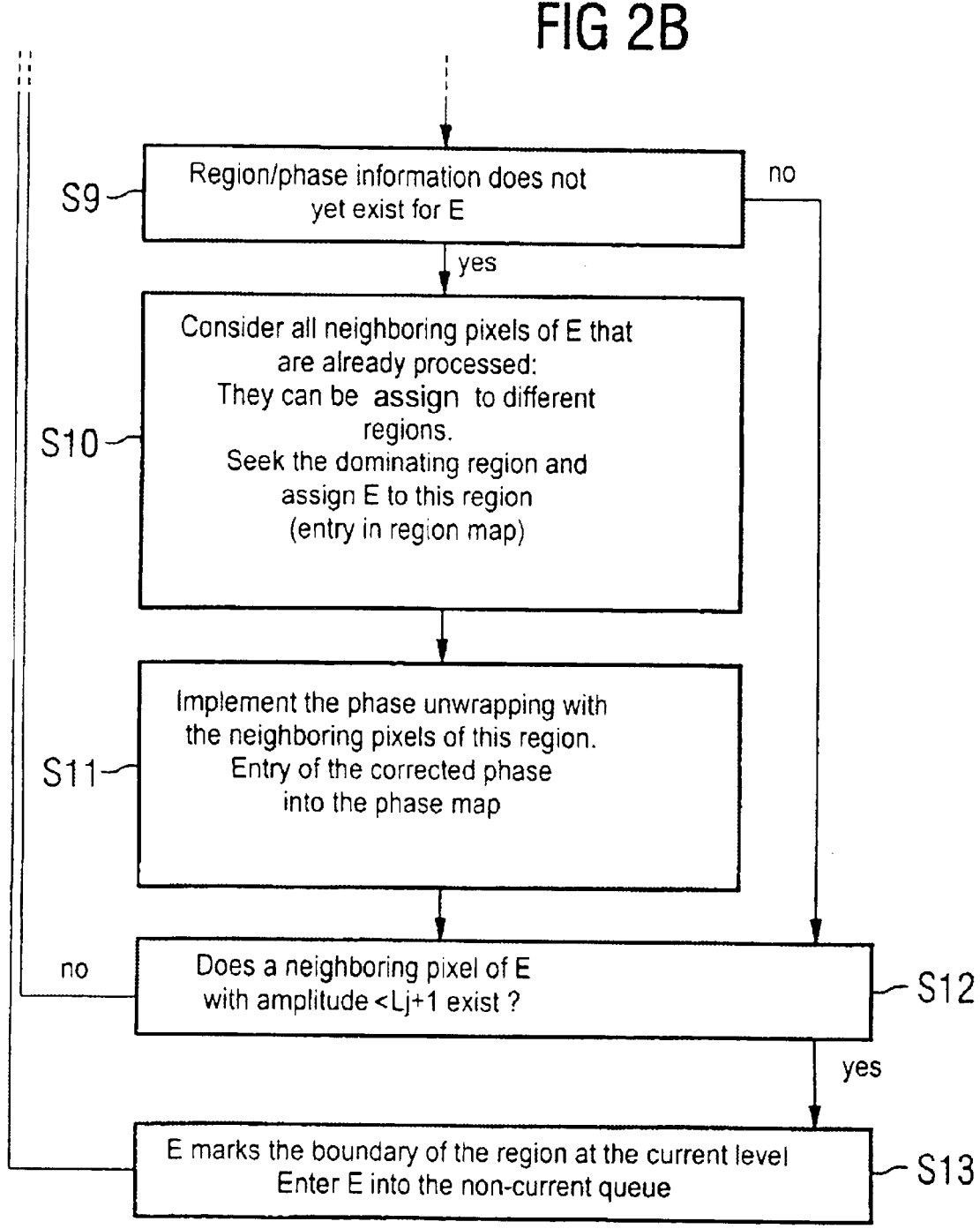

Intensity Map:

1.

2.

3.

MAGNETIC RESONANCE METHOD AND APPARATUS FOR GENERATING RESPECTIVE IMAGES FROM SPIN ENSEMBLES EXHIBITING DIFFERENT CHEMICAL SHIFT

BACKGROUND OF THE INVENTION

1. Field of the Invention

The present invention is directed in general to magnetic resonance tomography (MRT) as employed in medicine for examining patients. The present invention is particularly directed to a nuclear magnetic resonance apparatus as well as to a method for the operation thereof of the type wherein, respective images based on spin collectives exhibiting different chemical shifts are obtained.

2. Description of the Prior Art

Magnetic resonance tomography is a tomographic method for medical diagnostics that is distinguished by a high contrast resolution capability. Due to the excellent presentation of soft tissue, nuclear magnetic resonance tomography has developed into a method that is often superior to x-ray computed tomography. Magnetic resonance tomography is currently based on the application of spin echo sequences and gradient echo sequences that enable an excellent image quality with measuring times on the order of magnitude of minutes.

In the presentation of the tissue of a patient, however, artifacts that arise from the influence of the chemical shift occur at the boundary layers between fat and water. Chemical shift is the phenomenon that the resonant frequency shifts slightly, proportional to the field strength, dependent on the type of chemical bond in which the atom containing nucleus participates. Due to its concentration in the human body, it is namely hydrogen nuclei of free water and of fat that contribute to the image. Their relative resonant frequency difference amounts to approximately 3 ppm (parts per million). The frequency difference leads to a relative shift of the images of the two spin type in the direction of the gradient that is active during the data acquisitions (read gradient or frequency coding gradient). The extent of the shift is dependent on the readout bandwidth per pixel, and thus on the field of view (FOV), and on the matrix size, among other things.

The original publication of W. T. Dixon, "Simple Proton Spectroscopic Imaging", which appeared in 1984 in Radiology, Volume 153, pages 189–194, presented a method that achieves a separation of fat images and water images with two echos (gradient or spin echos). Dixon's idea for separating the image information of fat and water on the basis of the chemical shift shall only be discussed herein to the extent necessary for an understanding of the inventive method and algorithm set forth below.

The basis of the separation of the fat signal and the water signal according to the Dixon method is the chemical shift between fat protons and water protons. As mentioned above, this leads to different precession frequencies of the respective proton types. In a symmetrical spin echo experiment, phases that evolved due to chemical shift (or due to magnetic field inhomogeneities as well) are re-focused. Fat and water magnetization ideally are parallel to one another at the point in time of the echo. This condition can then be intentionally changed precisely such that fat and water magnetization reside perpendicular or anti-parallel relative to one another at the point-in-time of the echo. This is achieved, for example, by shifting the refocusing pulse by a time $\Delta T = \pi / 2 \Delta \omega$ (anti-parallel), or by $\Delta T = \pi / 4 \Delta \omega$ (perpendicular relative to one another) ($\Delta \omega$ is the difference of the radian frequencies of fat and water protons due to the chemical shift). Of course, the relative magnetization orientations can also be generated with a suitable gradient echo sequence. When these three situations are then realized, i.e. when images are acquired with the corresponding phase evolution times, then the spin types can be locally prepared with phase relationships 0°, 90°, 180°. When the corresponding Fourier transformations are performed, three complex images are obtained that are composed of the spatially-dependent proton density of water ($W((\vec{r}))$) and fat ($F(\vec{r})$):

$$S_0 = (W(\vec{r}) + F(\vec{r})) \exp(i\Phi_0(\vec{r}))$$

$$S_1 = (W(\vec{r}) + iF(\vec{r})) \exp(i\Phi_0(\vec{r}) + \Phi(\vec{r})/2))$$

$$S_2 = (W(\vec{r}) - F(\vec{r})) \exp(i(\Phi_0(\vec{r}) + \Phi(\vec{r})))$$

$S_0$ is the magnetization when water and fat are in-phase, i.e. exhibit an angle of 0° relative to one another. $S_1$ is the magnetization at 90°, $S_2$ the magnetization at 180°. $\Phi_0$ denotes the system-conditioned, spatially-dependent phase that has already built up in the first image due to $B_1$ inhomogeneities of the excitation coils or due to the signal processing time in the spectrometer.

In the original Dixon method, only the images of parallel as well as anti-parallel alignment of the spin types relative to one another were employed, without taking field inhomogeneities into consideration. Algorithms for phase unwrapping of interconnected pixel regions (phase unwrapping) were developed in following publications by means of which field inhomogeneities could in fact be taken into consideration for the first time. These algorithms, however, were susceptible to error due to a region growth over regions having low signal-to-noise ratio. Phase unwrapping algorithms wherein the phase information were extrapolated over image regions without signal information proved equally susceptible to error. A good approach is represented by methods that (as above) initially enabled a pixel-by-pixel allocation of fat and water on the basis of parallel, anti-parallel and perpendicularly residing magnetization vectors and allowed a subsequent correction on the basis of local region growth. However, these methods have the disadvantage that the information available is not maximally utilized.

SUMMARY OF THE INVENTION

Since diagnostic information often can be acquired better from the image of a single spin collective, i.e. a pure water image or a pure fat image, it is an object to the present invention to provide a magnetic resonance tomography apparatus and a method wherein the signal contribution of a particular spin collective is suppressed, and thus separate images of two spin collectives chemically shifted relative to one another are generated.

It is a further object of the present invention to provide such a method and apparatus that use the maximum of the information available in order to be able to accomplish the classification of two spin collectives (for example, fat and water) in a simple way.

The starting point of the invention is a three-point Dixon method wherein 0°, 90° and 180° images are registered. The standard three-point Dixon method uses 0°, 180° and 360°— the relevancy of the 90° image shall become apparent later. Since the acquisition of a 0° image is not possible in a gradient echo sequence (by contrast to the spin echo), use is made of images having the magnetization phase position n*360°+0°/+90°/+180°.

To assist in explaining the invention, the way in which the phase evolution within a given (fixed) evolution time is dependent on the inhomogeneity is presented again, i.e. to show how the above three equations for $S_0$, $S_1$, $S_2$ are derived.

In a specific image pixel at the location ($\vec{r}$), let the proton density of the first type (water) amount to $W(\vec{r})$, and the proton density of the second type (fat) amount to $F(\vec{r})$. Let the difference of the precession frequency of both components amount to $\Delta\omega_{cs}$. A (time-constant) phase offset $\Phi_0(\vec{r})$ exists as a consequence of system-dependent phenomena. Further, the basic magnetic field is shifted by $\Delta B(\vec{r})$ compared to a reference point (inhomogeneity of the magnetic field). The two signal components (spin collectives 1 and 2) can be considered separately in their phase evolution:

For water, the phase evolution during a precession duration t can be described as:

$$\phi_1(\vec{r}) = \phi_0(\vec{r}) + \gamma \Delta B(\vec{r}) t$$

wherein $\gamma$ is the gyromagnetic ratio of the nucleus in question (hydrogen in this case).

A phase evolution of $$\phi_2(\vec{r}) = \phi_0(\vec{r}) + \gamma \Delta B(\vec{r}) t + \Delta\omega_{cs} t$$

is found for fat. The measured, super-positioned signal follows as $$S(\vec{r}, t) = W(\vec{r}) \exp(\phi_1(\vec{r} t)) + F(\vec{r}) \exp(i\phi_2(\vec{r}, t))$$

$$= (W(\vec{r}) + F(\vec{r}) \exp(i\Delta\omega_{cs} t)) \exp(i\phi_0(\vec{r})) \exp(i\gamma \Delta B(\vec{r}) t)$$

For $t_{180°} = \pi/\Delta\omega_{cs}$ with $\phi(\vec{r}) = \gamma \Delta B(\vec{r}) \pi/\Delta\omega_{cs}$:

$$S_2(\vec{r}) = (W(\vec{r}) - F(\vec{r})) \exp(i\phi_0(\vec{r})) \exp(i\gamma \Delta B(\vec{r}) \pi/\Delta\omega_{cs}))$$

$$= (W(\vec{r}) - F(\vec{r})) \exp(i\phi_0(\vec{r})) \exp(i\phi(\vec{r}))$$

For $t_{90°} = \pi/2\Delta\omega_{cs}$:

$$S_1(\vec{r}) = (W(\vec{r}) + iF(\vec{r})) \exp(i f_0(\vec{r})) \exp(if(\vec{r})/2)$$

The phase evolution $\phi(\vec{r})/2$ as well as $\phi(\vec{r})$ reflects the influence of basic field ($B_0$) inhomogeneities with a given (fixed), effective evolution time (for example, $t_{180°} = \pi/\Delta\omega_{cs}$ or $t_{90°} = \pi/2\Delta\omega_{cs}$, wherein t is the precession duration and $\Delta\omega_{cs}$ is the difference in the precession frequency of the two spin collectives.

The objective is then to determine $\Phi_0(\vec{r})$ as well as $\Phi(\vec{r})$ from the image data in order to thus eliminate the phase terms from the equation system. Pure water images and pure fat images then can be calculated from $S_0+S_2$ and $S_0-S_2$, respectively.

The unwrapping of the phases over interconnected pixel regions (phase unwrapping) represents the main problem given this procedure since the continuous variable $\Phi(\vec{r})$ can only be exactly determined to 180° only from the image information due to the periodicity of the complex exponential function. A precision of 360°, however, is necessary for unambiguous classification.

Thus, the above object is achieved in accordance with the invention in a magnetic resonance tomography apparatus that allows a fat image or a water image to be generated in a nuclear magnetic resonance tomography scan, using devices for generating a spin echo pulse sequence or gradient echo pulse sequence to which a subject to be examined is exposed. On the basis of a suitable combination of RF and gradient pulses (pulse sequences), the magnetization of the fat or water spin type at the respective echo time reside parallel, perpendicular and anti-parallel relative to one another and, following corresponding Fourier transformation, three complex images $S_0$, $S_1$, $S_2$ are thus obtained that are composed of the spatially-dependent proton density of water and fat and, beyond a system-dependent, spatially-dependent evolution phase $\Phi_0$, respectively have different evolution phases on the basis of $B_0$-field inhomogeneities characterized by different phases $\Phi/2$ and $\Phi$, respectively. Following the correction of $\Phi_0$, the correction of $\phi$ pursues, as does a subsequent fat-water classification in order to calculate a pure water image or a pure fat image from the three complex images.

The above object also is achieved in accordance with the invention in a method for obtaining a fat or water image in a nuclear magnetic resonance tomography scan wherein a spin echo or gradient echo pulse sequence is generated and the subject to be examined is exposed thereto, with suitable combinations of RF and gradient pulses (pulse sequences) causing the magnetization of the fat or water spin types at the respective echo time to reside parallel, perpendicular and anti-parallel relative to one another. After corresponding Fourier transformation, the acquisition of three complex images $S_0$, $S_1$, $S_2$ pursues, these being composed of the location-dependent proton density of water and fat and, beyond a system-dependent, location-dependent evolution phase $\Phi_0$, respectively comprising different evolution phases due to $B_0$ field inhomogeneities, characterized by different phases $\Phi/2$ and $\Phi$, respectively. After receiving the images, the correction of $\Phi_0$ is first undertaken, followed by the correction of $\Phi$ and, last, the fat-water classification.

In the inventive method and apparatus, the phase correction thus is undertaken in three steps:

1. Correction of $\Phi_0(\vec{r})$.
2. Correction of $\Phi(\vec{r})$,
3. Classification fat/water.

In the following, the $\Phi_0(\vec{r})$-corrected image is characterized by a notation with a single prime and the $\Phi_0(\vec{r})-\Phi(\vec{r})$ and corrected image is characterized by a notation with a double prime.

The phase factor $\Phi_0$ that is the same for all images is thus corrected first. The $\Phi_0$ correction thereby takes on a simple form: the corresponding phase map is supplied by the 0° image directly as $\text{Arg}(S_0)$. By rotation in the complex plane, each of the three datasets is corrected:

$$S'_0 = (W(\vec{r}) + F(\vec{r}))$$

$$S'_1 = (W(\vec{r}) + iF(\vec{r})) \exp(i\Phi(\vec{r})/2))$$

$$S'_2 = (W(\vec{r}) - F(\vec{r})) \exp(i\Phi(\vec{r}))$$

In multichannel acquisitions, i.e. acquisitions with a number of reception coils (channels), there is often a deviant spatial distribution of the phase response of the coils, so that an exact $\Phi_0$ correction is no longer possible after summed 0°/90°/180° images. A separate $\Phi_0$-correction therefore is useful for each individual channel—i.e. before the summation but following the Fourier transformation.

The image information $S'_2$ is used for determining the phase $\Phi(\vec{r})$. The sign of the amplitude factor is eliminated by squaring:

$$S'_2{}^2 = (W(\vec{r}) - F(\vec{r}))^2 \exp(i2\Phi(\vec{r}))$$

The phase of $S'_2{}^2$ initially yields the doubled inhomogeneity phase $2\Phi$ that can be determined location-dependently (due to the periodicity of the exponential function) except for an additive constant $n*2\pi$. The doubled phase angle value thus lies in the interval $[-\pi, \pi]$. The problem is now to unwrap the phase, i.e. to expand this value range to $[-\infty, \infty]$.

The solution to this problem is based on a new phase unwrapping algorithm that differs from known phase unwrapping algorithms essentially in that, proceeding from a seed point, a region of unwrapped phase is not grown to the noise level; instead a number of disjunctive regions are successively grown to a level that is steadily decreasing. As a result, the phase information that is well-defined in regions of high amplitude is maximally utilized. In the following step, the consistency of the fat-water classification is assured in all regions. In contrast to known algorithms, thus, there is no necessity to grow each region of interconnected image information down to the noise.

This new algorithm strives to determine the local, double inhomogeneity phase $2\Phi$ by considering the phases of a number of neighboring pixels. The underlying assumption is that no phase discontinuity greater than $\pi$ occurs between neighboring pixels, i.e. that the basic field is not too inhomogeneous. On this basis, proceeding from pixels having high signal amplitude, regions are allowed to grow by successive comparison to neighboring pixels wherein no phase discontinuity occurs. As soon as a phase discontinuity greater than $\pi$ occurs between two pixels, this is interpreted as a "wraparound" of the phase. Such phase discontinuities are eliminated by addition or subtraction of multiples of $2\pi$ and the phase $2\Phi$ is unwrapped within each region.

The result of this procedure is a map that contains a series of disjunctive regions with unwrapped phase. The phase relationship between the regions, however, is not unambiguously defined at this point in time; the existence of a phase discontinuity by multiplies of $\pi$ is still possible. It is only in the next step that this point is solved and the unambiguous classification of fat and water is simultaneously accomplished.

DESCRIPTION OF THE DRAWINGS

FIGS. 2A and 2B, in combination form a flowchart of the inventive algorithm;

DESCRIPTION OF THE PREFERRED EMBODIMENTS

Figure 1:
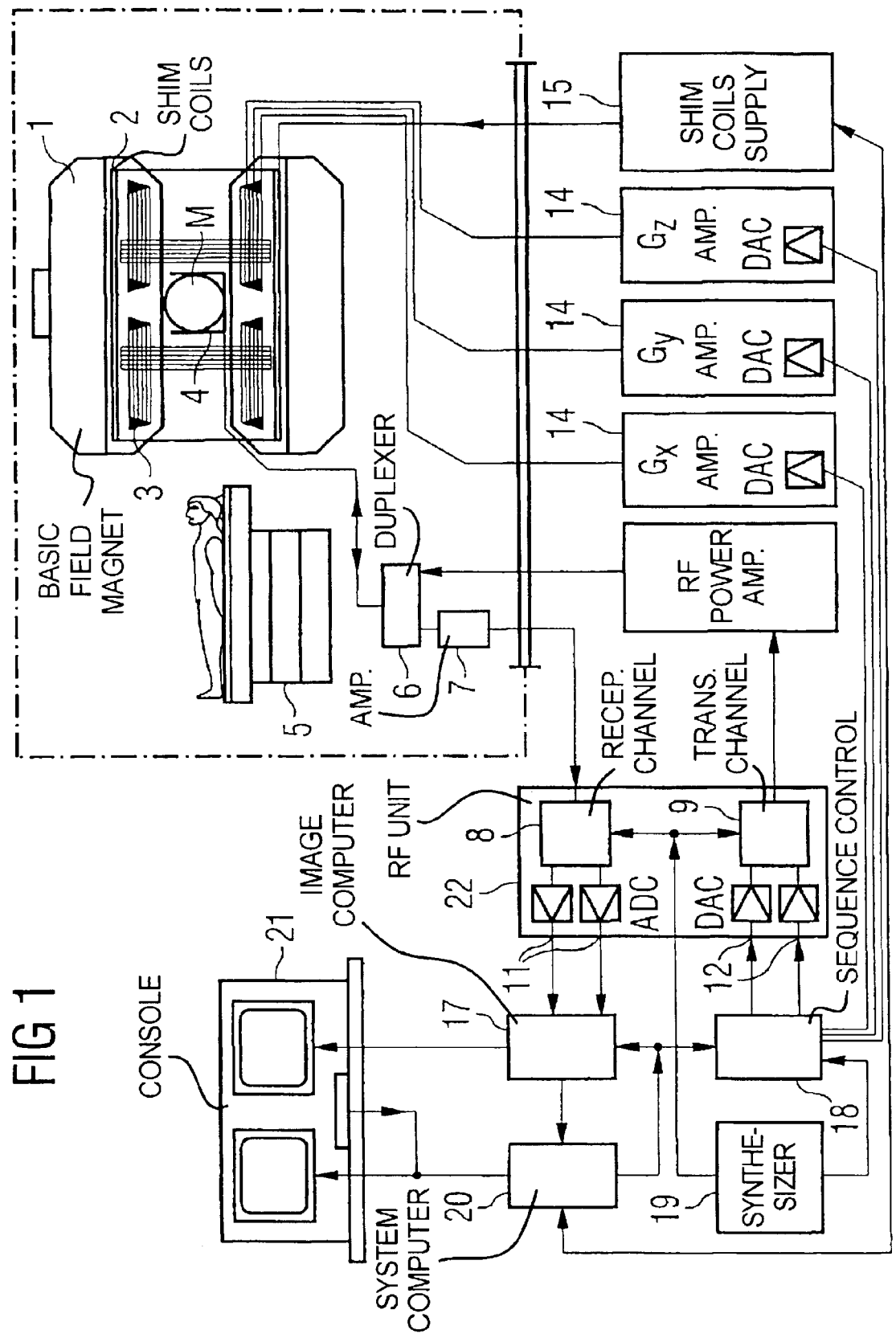
FIG. 1 is a schematic illustration of a magnetic resonance tomography apparatus constructed and operating in accordance with the invention.

FIG. 1 shows a schematic illustration of a magnetic resonance tomography apparatus for generating a nuclear magnetic resonance image of a subject according to the present invention. The basic components of the magnetic resonance tomography apparatus are conventional, but the apparatus is controlled to operate in accordance with the invention. A basic field magnet 1 generates a temporally constant, strong magnetic field for polarization or alignment of the nuclear spins in the examination region of a subject such as, for example, a part of a human body to be examined. The high-homogeneity of the basic magnetic field required for the magnetic resonance measurement is defined in a spherical measurement volume M into which the parts of the human body to be examined are introduced. For supporting the homogeneity demands and, in particular, for eliminating time-invariable influences, shim plates of ferromagnetic material are attached at suitable locations. Time-variable influences are eliminated by shim coils 2, that are driven by a shim power supply 15.

A cylindrical gradient coil system 3, for example, is introduced into the basic field magnet 1, this being composed of three partial windings. Each partial winding is supplied by an amplifier 14 with current for generating a linear gradient field in the respective direction of the Cartesian coordinate system. The first partial winding of the gradient field system 3 thereby generates a gradient $G_x$ in the x-direction; the second partial winding generates a gradient $G_y$ in the y-direction; and the third partial winding generates a gradient $G_z$ in the z-direction. Each amplifier 14 has a digital-to-analog converter that is driven by a sequence control 18 for the timed generation of gradient pulses.

A radio frequency antenna 4 (or a number of radio-frequency antennas 4 in the case of a multi-channel acquisition) is located within the gradient field system 3, which converts the radio-frequency pulses emitted by a radio-frequency power amplifier 30 into an alternating magnetic field for exciting the nuclei and for aligning the nuclear spins of the subject to be examined, or of the region of the subject to be examined. Each antenna 4 generally has its own ADC path for the real part and for the imaginary part. The alternating field emanating from the precessing nuclear spins, i.e. the nuclear magnetic resonance echo signals (usually produced by a pulse sequence composed of one or more radio-frequency pulses and one or more gradient pulses) is converted into a voltage by the radio-frequency antenna 4, this voltage being supplied via an amplifier 7 to a radio-frequency reception channel 8 of a radio-frequency system 22. The radio-frequency system 22 also has a transmission channel 9 in which the radio-frequency pulses are generated for the excitation of the nuclear magnetic resonance. The respective radio-frequency pulses are represented digitally as a sequence of complex numbers on the basis of a pulse sequence in the sequence control 18 prescribed by the system computer 20. The real part and the imaginary part, of this number sequence are respectively supplied via an input 12 to a digital-to-analog converter in the radio-frequency system 22 and from there to a transmission channel 9. In the transmission channel 9, a radio-frequency carrier signal, whose base frequency corresponds to the resonance frequency of the nuclear spins in the measurement volume, is modulated onto the pulse sequences.

The switching from transmission mode to reception mode is realized by a transmission/reception diplexer 6. The radio-frequency antenna 4 emits the radio-frequency pulses for exciting the nuclear spins into the measurement volume M and samples the resulting echo signals. The acquired nuclear magnetic resonance signals are demodulated in phase-sensitive fashion in the reception channel 8 of the radio-frequency system 22 and are converted via respective analog-to-digital converters into the real part and the imaginary part of the measured signal. An image is reconstructed with an image computer 17 from the measured data acquired in this way. The administration of the measured data, the image data and the control programs ensues via the image computer 17 or system computer 20. On the basis of a feedings with control programs, the sequence control 18 operates the generation of the desired pulse sequences and the corresponding sampling of k-space. In particular, the sequence control 18 controls the timed switching of the gradients, the application of the radio-frequency pulses with defined phase and amplitude, as well as the reception of the nuclear magnetic resonance signals. The time base for the radio-frequency system 22 and the sequence control 18 is made available by a synthesizer 19. The selection of corresponding control programs for generating a magnetic resonance image as well as the presentation of the generated magnetic resonance image takes place via a console 21 that has a keyboard as well as one or more picture screens.

Figure 2A:
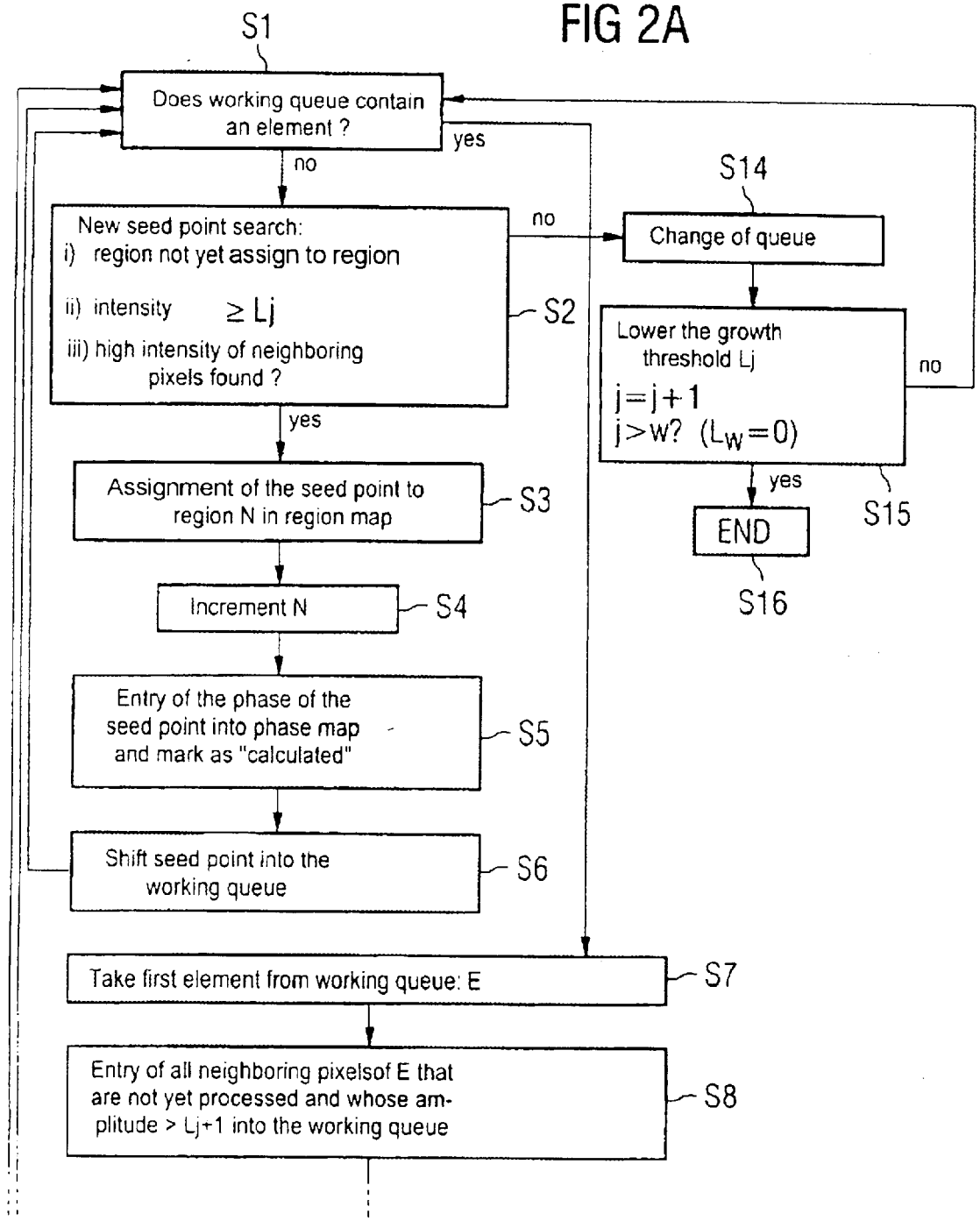

The inventive algorithm shall now be described on the basis of the flowchart in FIGS. 2A and 2B, this essentially supplying a phase map of disjunctive (unwrapped) regions (i.e., the unwrapped phase information and the corresponding information about the region to which a pixel is assigned).

Above all, the basis for the phase unwrapping is the $S_2$-image obtained by the image computer 17 in the form of a two-dimensional array of complex numbers. After the $\Phi_0$ correction on the basis of the $S_0$ image, which is likewise implemented in the image computer 17, only the $S_2$-image is required for the calculation of the phase map. Only after the end of the algorithm are the $S_0$-images and $S_1$-images required for calculating the fat images and water images, i.e., for the fat-water allocation. This likewise happens in the image computer 17 or a system computer.

Two FIFO memories—queues Q1 and Q2 implemented as software in the image computer 17, are employed for storing the coordinate pairs of the respective pixels.

The calculated phase $\Phi$ is entered into a two-dimensional array of real numbers, referred to as the phase map ($\Phi$-map). For each point of this map, there is also a flag that describes whether the correct phase has already been calculated.

The assignment of the pixels to a region is realized in a two-dimensional array of natural numbers—referred to as the region map—that contains the assigned region for each pixel, or zero if an assignment to a region has not yet been carried out.

At the beginning of the algorithm, the region map contains only zeros; the status in the phase map for all pixels is "phase not yet calculated", Q1 and Q2 are empty, the current queue (i.e., the working queue) is Q1.

Since no element is yet contained in the working queue in Step S1 at the beginning of the algorithm, a first seed point must initially be found in Step S2.

First, a search for the least average pixel intensity is made in a 5×5 pixel ROI at the border of the registered 180° image. This is assumed as the noise limit after multiplication by the factor 2. Next, a histogram is produced for all pixels having a higher amplitude. The intensity thresholds $L_j$, j=1, 2..., de-incremented successively in the growth process are derived from the rule that, for example, 10% of the pixels additionally lie above the threshold with every step. As soon as a level below the noise limit has been reached, zero is immediately used as the growth boundary.

The first seed point cannot yet be allocated to any region; it must exceed an intensity threshold $L_j$ (at the start: j=1) calculated according to the above method. Among the pixels with the amplitude >$L_j$, that pixel is selected for which the sum of its own amplitude and that of the eight neighboring pixels is maximum. When a point has thus been found, then this is allocated to a region—i.e. to region 1 at the start—in Step S3. The region counter N is incremented by 1 in Step S4. The phase of the seed point is entered into the phase map; the flag is correspondingly marked as "calculated". In Step S6, this seed point is shifted into the working queue.

Since the working queue now contains an element, namely the first seed point, this seed point E is taken from the working queue in Step S7 and, in Step S8, all neighboring pixels of E that were not yet processed when Step S8 was reached for the first time are entered in to the working queue—assuming their amplitudes exceed a certain minimum limit $L_{j+1}$ according to the above method. It should be noted that each pixel has eight neighbors: above, below, left, right, upper left, upper right, bottom left, bottom right. The algorithm, however, would also work with four neighbors (top, bottom, left, right).

When Step S8 is reached for the first time, a region and a corresponding phase information are present, so that Step S9 is followed by Step S12 wherein it is checked whether neighboring pixels of E having an amplitude smaller than $L_{j+1}$ exist at all. If E has at least one such neighboring pixels, E marks the boundary of the region of the current level $L_{j+1}$. In Step S13, E is therefore entered into the non-current queue. The next step is again S1.

It may occur in the following runs of Step S9 that the current E is not yet assigned to any region, or phase information is not yet present for E. In Step S10, all neighboring pixels of E that have already been processed are therefore taken into consideration. These neighboring pixels can be assigned to various regions. E is then assigned to that region for which the sum of the amplitudes of the appertaining neighboring pixels is maximum, and the entry into the region map is done. In Step S11, the phase unwrapping is now implemented with the neighboring pixels of this region: the phase of the neighboring pixels already processed is compared to that of the current pixel. Given a phase difference greater than $\pi$, the value for n that is needed is defined in order to obtain a phase difference lower than $\pi$ by addition of n*$2\pi$ is determined. In case more then one value results for n, weighting is carried out with the amplitude of the neighboring pixel and the most probable value is taken.

As a result of Steps S1 through S13, all pixels above a specific amplitude are assigned to one or more disjunctive, phase unwrapped regions. If, however, no further seed points can be found in the prescribed amplitude range, then the queue is changed in Step S14, and the growth threshold $L_j$ is lowered in Step S15: j=j+1. Pixels are already situated in the new working queue—i.e., those that were identified as boundary in the most recent growth level. Before new regions are thus grown (using new seed points), it is assured that the already existing regions are initially grown farther proceeding from the edge. Only after this occurs, and with a reduced intensity threshold, are new seed points again sought in Step S2, these in turn forming new regions as a result of the further steps.

If, however, the zero boundary of the growth amplitude $L_w$=0 is reached, i.e. j>w, then all pixels are covered and the algorithm stops (Step S16).

This algorithm can be visualized as an image of islands in water. The water level is high in the first iteration, only a few peaks (maximum pixel amplitude) rise above the water level. These small islands with high amplitude and correspondingly high precision in the phase are processed, i.e. phase unwrapped. In the next iteration (changing the queue), the water level sinks, the islands become larger and further processing is carried out proceeding from the "beach" of the preceding iteration. This prevents regions being grown across pixels having low intensities. After lowering the water level, it is not only "old" islands that continue to grow proceeding from the beach; rather, newly emerging islands also are included.

Figure 3:
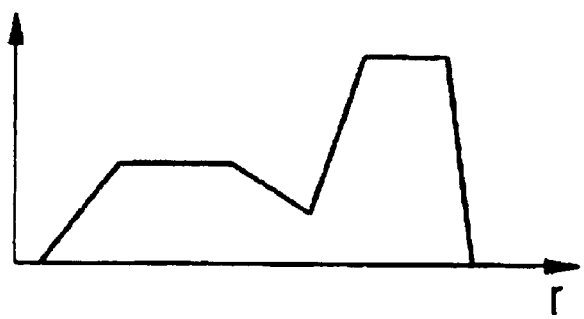
FIG. 3 schematically shows the intensity map in the curve of the algorithm.
Figure 3:
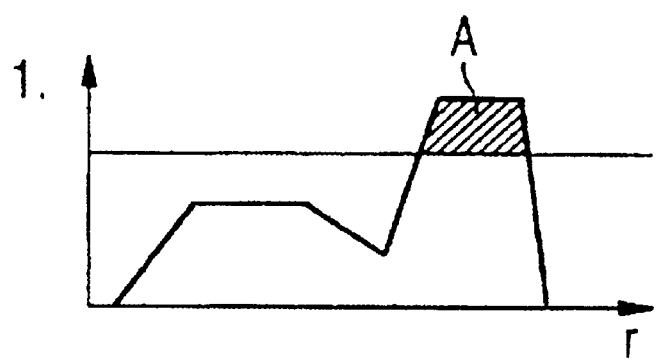
Figure 3:
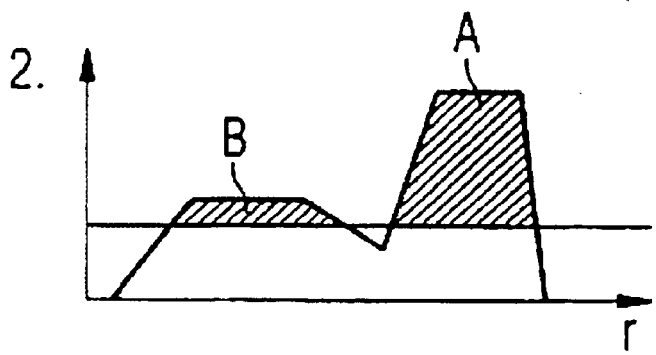
Figure 3:
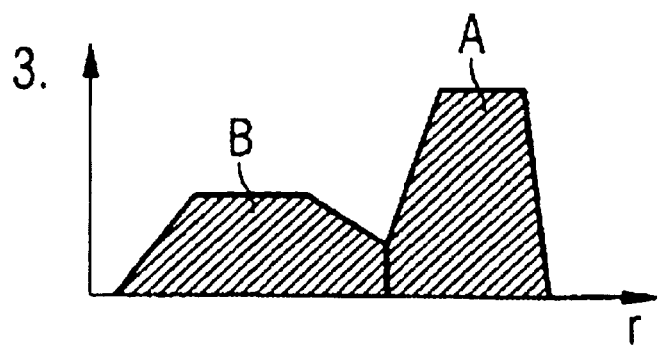

The result of this procedure, as shown in FIG. 3, is a map that contains a series of disjunctive regions, for example A and B, with unwrapped phase. The phase relationship between the regions, however, has not yet been unambiguously defined. A phase discontinuity by multiples of $\pi$ still is possible. It is only in the next step that this point is solved and the unambiguous classification of fat and water is simultaneously accomplished.

It is clear that no conclusion as to which of the two magnetization components is assigned to water and which is assigned to fat is possible on the basis of measurements with phase differences of $n*\pi$. It is known that the magnetization of the fat protons precesses more slowly and the rotational sense thereof in the rotating coordinate system of the water protons is thus evident. The rotational sense, however, cannot be derived from snapshots at 0° and 180°. An image at an intervening angle, for example 90°, is required for this purpose.

As mentioned above, the phase $\Phi$ cannot be precisely defined yet at $\pi$ for the first pixels of a region (i.e. the seed point). Since, however, the entire region is expanded proceeding from this point, this uncertainty is established for the entire region. The 180° $S_2'$ thus can be exactly corrected only to a multiple of $\pi$. A phase error of $\pi$, however, precisely corresponds to a change of the operational sign because $\exp(i\pi)=-1$, which would result in an interchange of fat and water. The phase map obtained on the basis of the $S_2'$ image (i.e. of the $\pi_0$-corrected 180° image) thus must have a multiple of $\pi$ added to it: $\Phi(\vec{r})+n\pi$. A value n must be individually determined for each region.

In order to unambiguously define the operational sign $S_2''$ (i.e. of the $\Phi_0$-corrected and $\Phi$-corrected 180° image), it suffices to know whether n is even or odd. This information is obtained from $S_1'$, the $\Phi_0$-corrected 90° image. However, the phase of $S_1'$ is only known to multiples of $\pi/2$; the phase correction here thus ensues by rotation by $$\Phi(\vec{r})/2+n\pi/2.$$

This yields four possible, relevant phase offsets of $S_1'$: 0, $\pi/2$, $\pi$, $3\pi/2$ (n=0, 1, 2, 3).

The objective is to compare, pixel-by-pixel, a 90° dataset calculated on the basis of the measured 0° and 180° images $$S_1'^T=(W^T+iF^T)e^{i\Phi T/2}$$

(i.e., the 90°-image that is to be expected without $\Phi$-correction but with $\Phi_0$-correction) to the measured $S_1'$ after rotation by each of the four possible phases. The index T indicates that the required quantities $W(\vec{r})$, $F(\vec{r})$ and $\Phi(\vec{r})$ are obtained not by direct measurement but by calculation.

Four solutions thus arise. That having the minimum deviation from what has been measured is interpreted as correct:

1. n=0
   $S_2'$ is corrected by $-\Phi$;
   $S_1'^T$ receives the phase $\Phi/2+0*\pi/2$;

$$\left.\begin{array}{l}S_0'=W+F\\S_2''=S_2'e^{-i\phi}=W-F\end{array}\right\}\begin{array}{l}W=1/2(S_0'+S_2'')\\F=1/2(S_0'-S_2'')\end{array}$$

$$S_1'^T=\frac{1}{2}[(S_0'+S_2'')+i(S_0'-S_2'')]e^{i\Phi/2}$$

2. n=1;
   $S_2'$ is corrected by $-(\Phi+\pi)$;
   $S_1'^T$ receives the phase $\Phi/2+1*\pi/2$;

$$\left.\begin{array}{l}S_0'=W+F\\S_2''=S_2'e^{-i(\phi+\pi)}=F-W\end{array}\right\}\begin{array}{l}W=1/2(S_0'-S_2'')\\F=1/2(S_0'+S_2'')\end{array}$$

$$S_1'^T=\frac{1}{2}[(S_0'-S_2'')+i(S_0'+S_2'')]e^{-i(\Phi/2+\pi/2)}$$

3. n=2;
   $S_2'$ is corrected by $-(\Phi+2\pi)$;
   $S_1'^T$ receives the phase $\Phi/2+2*\pi/2$;

$$\left.\begin{array}{l}S_0'=W+F\\S_2''=S_2'e^{-i(1+\phi)}=W-F\end{array}\right\}\begin{array}{l}W=1/2(S_0'+S_2'')\\F=1/2(S_0'-S_2'')\end{array}$$

$$S_1'^T=\frac{1}{2}[(S_0'+S_2'')+i(S_0'-S_2'')]e^{i(\Phi/2+\pi)}$$

4. n=3;
   $S_2'$ is corrected by $-(\Phi+3\pi)$;
   $S_1'^T$ receives the phase $\Phi/2+3*\pi/2$;

$$\left.\begin{array}{l}S_0'=W+F\\S_2''=S_2'e^{-i(\phi+\pi)}=F-W\end{array}\right\}\begin{array}{l}W=1/2(S_0'-S_2'')\\F=1/2(S_0'+S_2'')\end{array}$$

$$_1'^T=\frac{1}{2}[(S_0'-S_2'')+i(S_0'+S_2'')]e^{-i(\Phi/2+3\pi/2)}$$

The decision as to which phase offset (i.e., which n) is to be selected for a region is made by comparison to the measured 90°-image $S_1'$. To that end, exactly that $n\epsilon[0, 1, 2, 3]$ is determined for each pixel of a region for which the deviation $W_n=((Re(S_1'^T)-Re(S_1'))^2+((Im(S_1'^T)-Im(S_1'))^2)$ is minimal. For the following decision as to which n is to be selected for the entire region, only pixels that contain fat as well as water, but not in identical parts are taken into consideration. This is the case when both $\|S_0|-|S_1|\|$ as well as $\|S_0|-|S_2|\|$ lie above defined thresholds, for example 10%/5% of the pixel amplitude and $|S_2|$ likewise lies above a defined threshold, for example 10% of the amplitude $|S_0|$. For each $n\epsilon[0, 1, 2, 3]$, the sum of the amplitudes of those pixels is now determined within the region, for which this n was optimum. The n that receives the greatest weighting in the sum is assumed to be the most probable one for this region. By means of a rotation in the complex plane, each region in the image $S_2'$ can be corrected with the identified phase factor: $S_2''=S_2'e^{-i(\Phi+n\pi)}$. The addition of $S_0'$ and $S_2''$ then supplies a pure water image and the subtraction supplies a pure fat image.

In this procedure, however, there is the risk that only a few pixels that allow a meaningful identification of water and fat will be found within some regions. This can lead to a wrong classification of fat and water within these regions. There is the following strategy in this case:

The criteria for an unambiguous and meaningful classification of fat and water within a region are comprised therein that,
    a defined minimum number of pixels contains adequate amounts of fat and water with adequately different parts according to the above-defined criteria; and
    the weight of the most probable n lies above the second most probable n by a defined threshold.
if these criteria are not met, the union with neighboring regions is striven for in that a search is made for that neighboring region for which an optimally long boundary line proceeds with optimally high amplitude ($\Sigma A_i$ is maximum, whereby $\Sigma A_i$ is the sum of the amplitudes of those pixels that form the boundary between the current and a neighboring region).
in order to obtain a common unwrapped phase, it has to be determined for each pixel of the boundary line as to which multiple k of $\pi$. Subsequently, a decision is again made via the weighting with the pixel amplitudes as to which k is the most probable (since, of course, only one k can be correct insofar as both regions are correctly unwrapped). It must be emphasized in any case that the principle of "maximizing the information" is again applied.
possibly after a phase shift of the current region by $k\pi$, the two regions are united. Taking all fat-water information of both regions into consideration, a judgment is now made according to the above procedure as to whether adequate information are now present for fat-water classification. If this not yet the case, further regions must also be involved.

The processing of the magnetic resonance tomography images that were obtained thus has been ended. The addition of $S_0''$ and $S_2''$ supplies a pure water image and the subtraction supplies a pure fat image. The signal-to-noise ratio resulting from the images corresponds to that of two averagings. Fundamentally, the 90°-image—following corresponding phase correction by $e^{-i(\Phi/2+n^*\pi/2)}$—could also be calculated into the fat or, respectively, water images in order to thus obtain a S/N that corresponds to three averagings.

In the above-described growth procedure, no consideration was given to the size of the phase difference relative to the neighbors. This, however, means that growth proceeds over points having pronounced inhomogeneities. This can lead to incorrect classifications that propagate during the growth, even though usually only locally pronounced phase differences occur. In order to prevent this, a pixel is incorporated into the working queue only when the phase difference compared to currently processed neighbor lies below a threshold (for example, 90°). The pixel thus is not completely excluded from the growth process, since the criterion is re-examined as soon as growth is carried out from another neighboring pixel.

Lastly, the problems of a low signal-to-noise ratio (SNR) shall be discussed. The inventive algorithm stems, so to speak, from SNR. Problems can arise when the SNR is extremely low and work is carried out pixel-by-pixel in the correction of the constant phase as well as in the correction of the inhomogeneity phase. Since, however, the information of the phase map on a coarser grid suffices, it is expedient to implement an averaging (interpolation) before the beginning of the algorithm, in that the phase of an individual pixel is calculated with the assistance of its eight neighbors. A certain factor in the SNR that makes the algorithm more stable is thereby acquired. In order to identify the phase necessary for the algorithm to function, thus, it is not the original phase of the pixel that is taken but an average over a 3×3 pixel grid is formed. After the phase map has been calculated with a correspondingly coarser grid, the $S_1'$ and $S_2'$ images are corrected therewith. The smoothing is thus only utilized for the calculation of the phase map; the resolution of the fat and water images that are generated does not change.

Although modifications and changes may be suggested by those skilled in the art, it is the intention of the inventor to embody within the patent warranted hereon all changes and modifications as reasonably and properly come within the scope of his contribution to the art.

I claim:

1. A magnetic resonance tomography apparatus comprising:
    a magnetic resonance scanner adapted to receive a subject therein for exposing said subject to a basic magnetic field, exhibiting field inhomogeneities, and to a pulse sequence selected from the group consisting of spin echo pulse sequences and gradient echo pulse sequences, to excite a first spin ensemble and second spin ensemble in said subject, said first and second spin ensembles each exhibiting a magnetization and exhibiting respectively different chemical shift, said scanner obtaining nuclear magnetic resonance signals arising from both said first and second spin ensembles at respective echo times in said pulse sequence at which the respective magnetizations of said first and second spin ensembles reside perpendicularly, parallel and anti-parallel relative to each other; and
    a computer supplied with said nuclear magnetic resonance signals for Fourier transforming said nuclear magnetic resonance signals to obtain three complex images $S_0$, $S_1$ and $S_2$ respectively for said echo times, each of said complex images representing a location-coded proton density of said first and second spin ensembles and containing a location-dependent evolution phase $\Phi_0$ and different evolution phases $\Phi$ produced by said field inhomogeneities, said computer correcting said complex images for $\Phi_0$ to obtain $\Phi_0$-corrected images and subsequently correcting said $\Phi_0$-corrected images for $\Phi$ to obtain fully corrected complex images, and assigning respective contributions in said fully corrected complex images to said first and second spin ensembles to calculate at least one of a pure image of said first spin ensemble and a pure image of said second spin ensemble.

2. A magnetic resonance tomography apparatus as claimed in claim 1 wherein said image computer corrects said complex images for $\Phi_0$ by rotating said complex images $S_0$, $S_1$ and $S_2$ in the complex plane by $\Phi_0$ to obtain respective $\Phi_0$-corrected images $S_0'$, $S_1'$ and $S_2'$.

3. A magnetic resonance tomography apparatus as claimed in claim 1 wherein said scanner comprises a plurality of reception coils, and wherein each of said reception coils receive a respective set of said nuclear magnetic resonance signals, and wherein said image computer separately corrects said respective sets of nuclear magnetic resonance signals, after Fourier transformation thereof, for $\Phi_0$.

4. A magnetic resonance tomography apparatus as claimed in claim 1 wherein said $\Phi_0$-corrected images respectively contain pixels with no neighboring pixels exhibiting a phase discontinuity larger than a predetermined phase value, and wherein said computer corrects said $\Phi_0$-corrected images for $\Phi$ by identifying regions of pixels in $\Phi_0$ corrected images having a signal amplitude above a predetermined minimum value and wherein no phase discontinuity occurs and successively compares neighboring pixels to each other with corresponding phase unwrapping.

5. A magnetic resonance tomography apparatus as claimed in claim 4 wherein said computer determines pixels wherein no phase discontinuity occurs by including a pixel in said region if that pixel exhibits a phase difference from a neighboring pixel, already in said region, that is below a predetermined threshold.

6. A magnetic resonance tomography apparatus as claimed in claim 4 wherein said computer repeats the correction for $\Phi$ with a plurality of successively lowered minimum values determined from an automatic noise level estimate and an intensity histogram.

7. A magnetic resonance tomography apparatus as claimed in claim 6 wherein said computer corrects for $\Phi$ initially only in regions composed of pixels with a high signal amplitude, and incrementally generates regions containing pixels having signal amplitudes lower than said high signal amplitude.

8. A magnetic resonance tomography apparatus as claimed in claim 4 wherein said phase unwrapping produces a plurality of disjunctive phase-unwrapped regions, and wherein said computer subsequently makes an unambiguous determination of a most probable phase offset among said disjunctive phase-unwrapped regions.

9. A magnetic resonance tomography apparatus as claimed in claim 8 wherein said computer determines said most probable phase offset by a pixel-by-pixel mathematical comparison of a $\Phi_0$-corrected 90° image $S_1'$ to calculated and $\Phi_0$-corrected 90° images $S_1''$.

10. A magnetic resonance tomography apparatus as claimed in claim 9 wherein said computer sets a first criterion of a minimum number of pixels for said mathematical comparison that contain respective predetermined minimum contributions from said first and second spin ensembles, but not equal contributions.

11. A magnetic resonance tomography apparatus as claimed in claim 10 wherein said computer defines said most probable phase offset as a phase offset exhibited by most pixels in said region, and sets a second criterion of a number of pixels in said region having a second most probable phase offset as being a predetermined threshold below the number of pixels with the most probable phase offset.

12. A magnetic resonance tomography apparatus as claimed in claim 11 wherein said computer, if said first and second criteria are not met, merges two of said disjunctive regions to form an overall phase-unwrapped region dependent on a boundary between said two regions.

13. A magnetic resonance tomography apparatus as claimed in claim 7 wherein each of said regions exhibits a phase offset, and wherein said computer, dependent on the phase offset of a region, $\Phi$-corrects a $\Phi_0$-corrected 180° image $S_2$ by rotation in said complex plane to obtain a $\Phi$-corrected and $\Phi_0$-corrected 180° image $S_2''$.

14. A magnetic resonance tomography apparatus as claimed in claim 13 wherein said computer generates said at least one pure image as a pure image of said first spin ensemble by adding $S_0'$ and $S_2''$.

15. A magnetic resonance tomography apparatus as claimed in claim 13 wherein said computer generates said at least one pure image as a pure image of said second spin ensemble by subtracting $S_0'$ and $S_2''$.

16. A magnetic resonance tomography apparatus as claimed in claim 1 wherein said complex images contain pixels in a pixel grid, and wherein said computer smooths said $\Phi_0$-corrected images and said fully corrected images by interpolating pixels in a coarser pixel grid.

17. A magnetic resonance tomography apparatus as claimed in claim 1 wherein said first spin ensemble represents water in said subject and wherein said second spin ensemble represents fat in said subject.

18. A magnetic resonance tomography method comprising the steps of:

exposing a subject to a basic magnetic field, exhibiting field inhomogeneities, and to a pulse sequence selected from the group consisting of spin echo pulse sequences and gradient echo pulse sequences, to excite a first spin ensemble and second spin ensemble in said subject, said first and second spin ensembles each exhibiting a magnetization and exhibiting respectively different chemical shift, and obtaining nuclear magnetic resonance signals arising from both said first and second spin ensembles at respective echo times in said pulse sequence at which the respective magnetizations of said first and second spin ensembles reside perpendicularly, parallel and anti-parallel relative to each other; and Fourier transforming said nuclear magnetic resonance signals to obtain three complex images $S_0$, $S_1$ and $S_2$ respectively for said echo times, each of said complex images representing a location-coded proton density of said first and second spin ensembles and containing a location-dependent evolution phase $\Phi_0$ and different evolution phases $\Phi$ produced by said field inhomogeneities, and correcting said complex images for $\Phi_0$ to obtain $\Phi_0$-corrected images and subsequently correcting said $\Phi_0$-corrected images for $\Phi$ to obtain fully corrected complex images, and assigning respective contributions in said fully corrected complex images to said first and second spin ensembles to calculate at least one of a pure image of said first spin ensemble and a pure image of said second spin ensemble.

19. A magnetic resonance tomography method as claimed in claim 18 comprising correcting said complex images for $\Phi_0$ by rotating said complex images $S_0$, $S_1$ and $S_2$ in the complex plane by $\Phi_0$ to obtain respective $\Phi_0$-corrected images $S_0'$, $S_1'$ and $S_2'$.

20. A magnetic resonance tomography method as claimed in claim 18 comprising receiving sad nuclear magnetic resonance signals with a plurality of reception coils, with each of said reception coils receiving a respective set of said nuclear magnetic resonance signals, and comprising separately correcting said respective sets of nuclear magnetic resonance signals, after Fourier transformation thereof, for $\Phi_0$.

21. A magnetic resonance tomography method as claimed in claim 18 wherein said $\Phi_0$-corrected images respectively contain pixels with no neighboring pixels exhibiting a phase discontinuity larger than a predetermined phase value, and comprising correcting said $\Phi_0$-corrected images for $\Phi$ by identifying regions of pixels in $\Phi_0$ corrected images having a signal amplitude above a predetermined minimum value and wherein no phase discontinuity occurs and successively compares neighboring pixels to each other with corresponding phase unwrapping.

22. A magnetic resonance tomography method as claimed in claim 21 comprising determining pixels wherein no phase discontinuity occurs by including a pixel in said region if that pixel exhibits a phase difference from a neighboring pixel, already in said region, that is below a predetermined threshold.

23. A magnetic resonance tomography method as claimed in claim 21 comprising repeating the correction for $\Phi$ with a plurality of successively lowered minimum values determined from an automatic noise level estimate and an intensity histogram.

24. A magnetic resonance tomography method as claimed in claim 23 comprising correcting for $\Phi$ initially only in regions composed of pixels with a high signal amplitude, and incrementally generating regions containing pixels having signal amplitudes lower than said high signal amplitude.

25. A magnetic resonance tomography method as claimed in claim 21 wherein said phase unwrapping produces a plurality of disjunctive phase-unwrapped regions, and comprising subsequently making an unambiguous determination of a most probable phase offset among said disjunctive phase-unwrapped regions.

26. A magnetic resonance tomography method as claimed in claim 19 comprising determining said most probable phase offset by a pixel-by-pixel mathematical comparison of a $\Phi_0$-corrected 90° image $S_1'$ to calculated and $\Phi_0$-corrected 90° images $S_1''$.

27. A magnetic resonance tomography method as claimed in claim 26 comprising setting a first criterion of a minimum number of pixels for said mathematical comparison that contain respective predetermined minimum contributions from said first and second spin ensembles, but not equal contributions.

28. A magnetic resonance tomography method as claimed in claim 27 comprising defining said most probable phase offset as a phase offset exhibited by most pixels in said region, and setting a second criterion of a number of pixels in said region having a second most probable phase offset as being a predetermined threshold below the number of pixels with the most probable phase offset.

29. A magnetic resonance tomography method as claimed in claim 28 comprising, if said first and second criteria are not met, merging two of said disjunctive regions to form an overall phase-unwrapped region dependent on a boundary between said two regions.

30. A magnetic resonance tomography method as claimed in claim 24 wherein each of said regions exhibits a phase offset, and comprising, dependent on the phase offset of a region, $\Phi$-correcting a $\Phi_0$-corrected 180° image $S_2$ by rotation in said complex plane to obtain a $\Phi$-corrected and $\Phi_0$-corrected 180° image $S_2''$.

31. A magnetic resonance tomography method as claimed in claim 30 comprising generating said at least one pure image as a pure image of said first spin ensemble by adding $S_0'$ and $S_2''$.

32. A magnetic resonance tomography method as claimed in claim 30 comprising generating said at least one pure image as a pure image of said second spin ensemble by subtracting $S_0'$ and $S_2''$.

33. A magnetic resonance tomography method as claimed in claim 18 wherein said complex images contain pixels in a pixel grid, and comprising smoothing said $\Phi_0$-corrected images and said fully corrected images by interpolating pixels in a coarser pixel grid.

34. A magnetic resonance tomography method as claimed in claim 18 wherein said first spin ensemble represents water in said subject and wherein said second spin ensemble represents fat in said subject.

\* \* \* \* \*